(12) United States Patent
Power

(10) Patent No.: US 7,538,879 B2
(45) Date of Patent: May 26, 2009

(54) LIGHT PROFILE MICROSCOPY APPARATUS AND METHOD

(76) Inventor: Joan F. Power, 1100 Dr. Penfield, Apt. 822, Montreal, Quebec (CA) H3A 1A8

(*) Notice: Subject to any disclaimer, the term of this patent is extended or adjusted under 35 U.S.C. 154(b) by 363 days.

(21) Appl. No.: 10/599,227

(22) PCT Filed: Mar. 30, 2005

(86) PCT No.: PCT/CA2005/000467

§ 371 (c)(1),
(2), (4) Date: Dec. 7, 2006

(87) PCT Pub. No.: WO2005/096061

PCT Pub. Date: Oct. 13, 2005

(65) Prior Publication Data

US 2008/0218850 A1 Sep. 11, 2008

Related U.S. Application Data

(60) Provisional application No. 60/557,385, filed on Mar. 30, 2004.

(51) Int. Cl.
*G02B 21/06* (2006.01)
*G01N 21/84* (2006.01)
(52) U.S. Cl. ............... 356/438; 356/432; 359/385
(58) Field of Classification Search ......... 356/432–444, 356/628–630, 495; 359/385, 885; 250/330, 250/341.1–341.4; 430/5

See application file for complete search history.

(56) References Cited

U.S. PATENT DOCUMENTS

| | | | | |
|---|---|---|---|---|
| 5,272,342 A | * | 12/1993 | Kotani | 250/341.4 |
| 5,365,065 A | * | 11/1994 | Power | 250/330 |
| 5,995,223 A | * | 11/1999 | Power | 356/495 |
| 6,151,119 A | * | 11/2000 | Campion et al. | 356/630 |
| 6,331,368 B2 | * | 12/2001 | Dirksen et al. | 430/5 |

(Continued)

OTHER PUBLICATIONS

Fu, S.W. et al., "Broadband Light Profile Microscopy: A Rapid and Direct Method for Thin Film Depth Imaging", :96-104.

(Continued)

*Primary Examiner*—Sang Nguyen
(74) *Attorney, Agent, or Firm*—Francois Martineau

(57) ABSTRACT

An apparatus and method allowing an optimized illumination in a light profile microscope by excitation of a sample with an elliptically collimated beam. The beam, which is typically supplied by a laser is collimated with unequal beam waist radii (and Rayleigh ranges) along major and minor axes orthogonal to a propagation direction, and approximates a plane sheet of illumination. The plane sheet of illumination is aligned with a thinnest width dimension thereof along the optic axis of the microscope objective, and with a center thereof at the object plane of the objective. Excitation light in a test sample is thereby confined to within a narrow thickness of the object plane of the objective lens, which minimizes out-of focus light in the image. The major axis width of the plane illumination sheet is typically a factor of ten or more greater than the minimum width, allowing a large area of the test sample to be illuminated and imaged. This excitation arrangement optically emulates the operation of micro-toming a thin cross section of a material for analysis, and provides optimum resolution and field in a light profile microscope.

15 Claims, 4 Drawing Sheets

U.S. PATENT DOCUMENTS 6,614,532 B1     9/2003    Power et al.
2004/0012872 A1*   1/2004    Fleming et al. ............. 359/885

OTHER PUBLICATIONS

Power, Joan F. et al., "Longitudinal Light Profile Microscopy: A New Method for Seeing Below the Surfaces of . . .", Applied Spectroscopy (1999) vol. 53(12):1507-1519.

Power, Joan F. et al., "Dual Beam Light Profile Microscopy: A New Technique for Optical . . .", Applied Spectroscopy (2004) vol. 58(2):166-178.

Power, J.F., "Fresnel diffraction model for the point spread of a laser light profile microscope (LPM)", Appl. Phys. B 78 (2004), pp. 693-703.

Smith, Warren J., Modern Optical Engineering: The Design of Optical Systems, Second Edition, 1990, pp. 270-278, McGraw-Hill, New York.

* cited by examiner

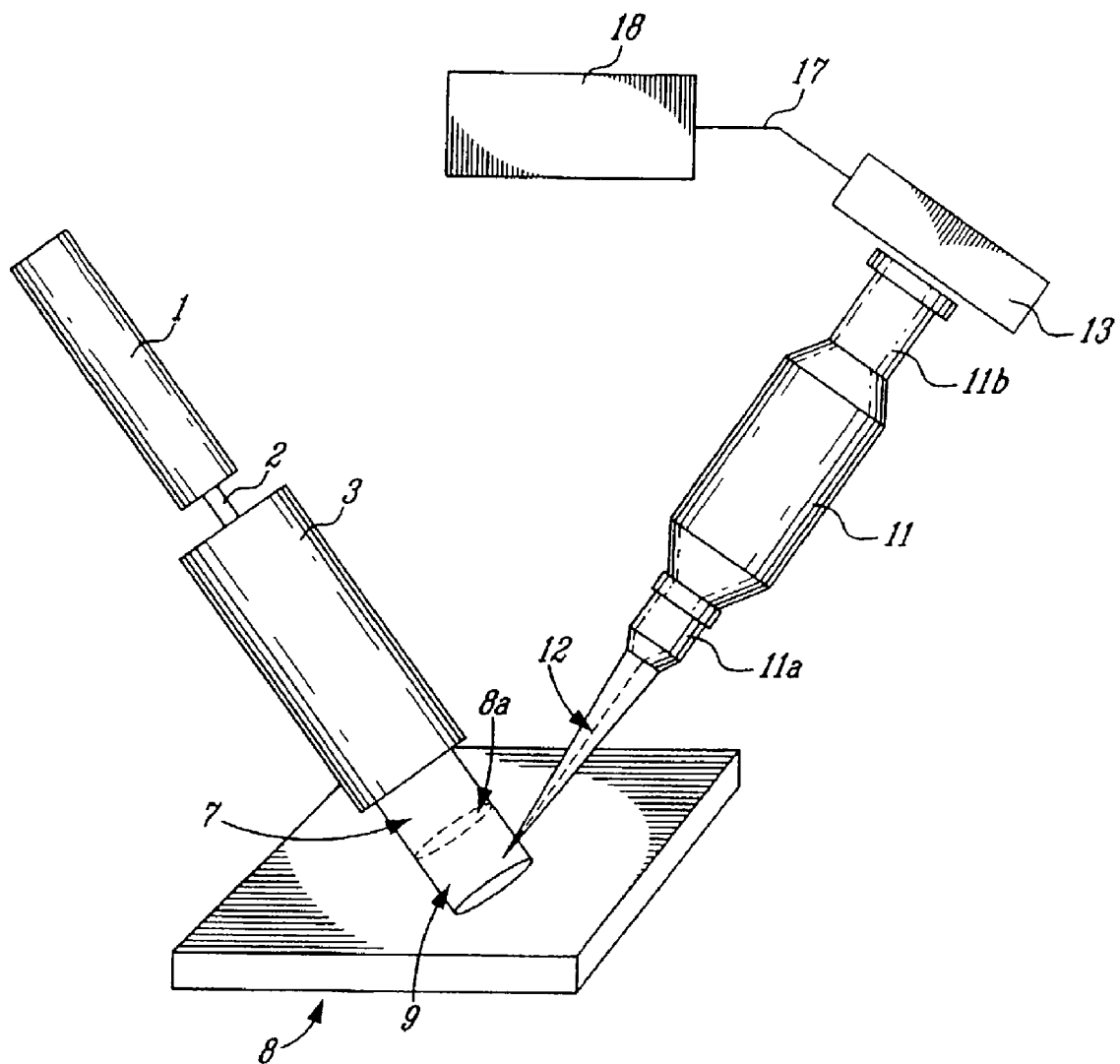
FIG_4

US 7,538,879 B2

LIGHT PROFILE MICROSCOPY APPARATUS AND METHOD

CROSS-REFERENCE TO RELATED APPLICATIONS

This application is a National Entry Application of PCT application no PCT/CA2005/000467 filed on Mar. 30, 2005 and published in English under PCT Article 21(2), which itself claims priority on U.S. provisional application No. 60/557,385, filed on Mar. 30, 2004. All documents above are herein in their entirety by reference.

FIELD OF THE INVENTION

The present invention relates to light profile microscopy (LPM). More specifically, the present invention is concerned with an apparatus and a method for illuminating a test material in a light profile microscope, so as to provide an optimized image resolution under broad field conditions.

BACKGROUND OF THE INVENTION

Light profile microscopy is an imaging method for obtaining direct images of cross sections of thin films using a light profile microscope (LPM) (see for example U.S. Pat. No. 6,614,532). The cross sectional images thus obtained may be used to identify the number, dimensions, composition and/or material morphology of individual layers making up the structure of a thin film test material for example. Light profile microscopy is to date a unique method for direct micrometer scale imaging of depth structures in thin layers, which may be conducted rapidly and with minimal modification and/or preparation of the test material. Light profile microscopy furthermore allows an image resolution that is close to or equal to the Rayleigh diffraction limit of an optical microscope as defined herein below (see relations 5 and 6 below).

In a standard set up for light profile microscopy, a material under test, referred to hereinafter as the test material, is usually, although not necessarily, a planar structure with major lateral dimensions and a depth dimension, along axes designated as 'y', 'z' and 'x' respectively. A beam of excitation radiation, referred to hereinafter as the source beam, is directed through the test material along the depth dimension 'x'. This beam is displaced along the 'z' axis behind a cross sectional surface of the test material, which may be an edge prepared by cleavage to expose the cross sectional structure of the thin film. This surface is referred to as the image transfer (IT) surface because radiation transferred through it is used to form an image of the excitation beam propagating behind it, inside the test material.

The IT surface is usually polished to prevent any optical defects present thereon from affecting the image. Image radiation is emitted from the source beam in the test material by light scattering, which may be elastic Rayleigh scatter, or inelastic Raman scatter, by luminescence (fluorescence and/or phosphorescence), or by other emission mechanisms, such as blackbody emission, for example, or by chemi-luminescence as excited thermally by the source beam. The image radiation is typically, although not exclusively, incoherent with the radiation in the source beam.

An optical imaging system (OIS) is used to form the light profile microscopy (LPM) image from the image radiation. The OIS typically comprises a combination of lenses and/or mirrors forming an image at an image plane. The OIS is aligned at ninety degrees to the depth axis 'x' along a direction normal to the IT surface, which typically corresponds to the 'z' direction, hereinafter referred to as the optic axis.

The LPM image is recorded with a spatial resolution that is close to the diffraction limit of the OIS, as set forth hereinbelow. The OIS is assumed to have its image resolution close to the diffraction limit. It is to be noted that the imaging properties of the OIS differ from those of macroscopic scale imaging systems. The latter systems have image resolution that is far from the diffraction limit and is limited severely either by optical aberrations or by the dimensions of the image pixels of a camera or image recording instrument.

The LPM image has a number of features characteristic of images recorded using an OIS in such an LPM layout. First, the limited object depth of focus of the OIS allows forming an image of the source beam, with the source beam aligned at a sufficient distance behind the IT surface, inside the test material, so that any scratches and defects in the IT surface are held significantly out of focus in the LPM image. It is to be noted that in the event that this condition is not strictly met, the LPM measurement is not invalid. Second, the orthogonal LPM geometry maintained between the depth axis 'x' and the optic axis 'z' yields a very high contrast in the LPM image for interfaces and boundaries in the cross section of the thin film test material. This image contrast is much greater than that available from images obtained using other microscopy methods known in the art. This orthogonal LPM geometry allows making direct imaging of depth structures in a material. Third, the image features of structures that scatter light in the direction of the OIS are emphasized in LPM images, in contrast to features that do not so scatter, which allows LPM images to record structures that may appear invisible in other prior art microscopy methods. This high scatter contrast may also have the effect of rendering insignificant scratches and defects in the IT surface and their contribution to LPM images that are recorded when the source beam is close to the IT surface.

A number of applications of light profile microscopy as a method of industrial thin film imaging are described in U.S. Pat. No. 6,614,532 by the present inventor for example, and in recent publications in the literature (see for example J. F. Power and S. W. Fu, Longitudinal Light Profile Microscopy (LLPM): A New Method for Seeing Below the Surfaces of Thin Film Materials *Applied Spectroscopy* 53(12), 1507-1519 (1999); S. W. Fu and J. F. Power, Broadband Light Profile Microscopy (BB-LPM): A Rapid and Direct Method for Thin Film Depth Imaging, *Applied Spectroscopy* 58, 96-104 (2004); J. F. Power and S. W. Fu, Dual Beam Light Profile Microscopy (LPM): A New Technique for Optical Absorption Depth Profilometry, *Appl. Spectros.* 58(2), 166-178, (2004)).

However, there is still a need in the art for a method and apparatus of light profile microscopy providing an optimized image resolution under broad field conditions.

SUMMARY OF THE INVENTION

More specifically, there is provided an apparatus for illuminating a test material in a light profile microscope, comprising a source of radiation providing a source beam propagating along a beam axis 'x'; an anamorphic optical means providing, from the source beam emitted by the source of radiation, a source beam elliptically collimated over an 'x' axial collimation region having a distance comprised in a range between micrometers and meters, and having a major elliptic axis oriented along a first transverse axis 'y', and a minor elliptic axis oriented along a second transverse axis 'z'; a test material positioned to intersect the elliptically collimated source beam within the 'x' axial collimation region to form an irradiated volume, the test material comprising an image transfer (IT) surface oriented substantially parallel to the 'x' axis and substantially orthogonal to the 'z' axis, the IT surface transmitting radiation emitted from the irradiated volume in the test material; an optical imaging system (OIS) forming an image, at an image plane, of the illuminated volume in the test material from the radiation transmitted by the IT surface; the OIS defining an object plane conjugate to the image plane and aligned to contain the major elliptic axis 'y' of the collimated source beam intersecting the test material in the illuminated volume, an object depth of focus of the OIS being maintained at a value of approximately at least ⅕ of a radius of the elliptically collimated source beam along the 'z' axis in the axial collimation region of the elliptically collimated source beam; and image receiving means receiving the image formed by the OIS in the image plane thereof; wherein the apparatus yields a high image resolution and wide image field.

There is further provided a method for illuminating a test material in a light profile microscope comprising a source of radiation, an anamorphic collimator, an optical imaging system and an image recording means, the method comprising the steps of propagating a source beam emitted by the source of radiation along a beam propagation axis 'x'; elliptically collimating the source beam along orthogonal axes 'y' and 'z' transverse to the beam propagation axis 'x' to yield a elliptically collimated source beam over an 'x' axial collimation region having a distance comprised in a range between microns and meters, and having a major elliptic axis oriented along the transverse axis 'y' and a minor elliptic oriented along the transverse axis 'z'; intersecting the elliptically collimated source beam within the 'x' axial collimation region with a test material to form an irradiated volume in the test material by said intersecting, and aligning an image transfer (IT) surface of the test material substantially parallel to the 'x' axis of the elliptically collimated source beam and substantially orthogonal to the 'z' axis of the elliptically collimated source beam; collecting an image radiation emitted from the irradiated volume in the test material and transmitted through the IT surface by an optical imaging system (OIS); forming an image at a fixed image plane with the OIS by aligning an object plane thereof conjugate to the image plane thereof at a central axis of the irradiated volume in the test material; maintaining an object depth of focus of the OIS at a value that is approximately at least ⅕ of a radius along the 'z' axis of the elliptically collimated source beam in the 'x' axial collimation region; and recording the image formed by the OIS in the image plane.

Other objects, advantages and features of the present invention will become more apparent upon reading of the following non-restrictive description of embodiments thereof, given by way of example only with reference to the accompanying drawings.

BRIEF DESCRIPTION OF THE DRAWINGS

In the appended drawings:

FIG. 4 is a schematic set-up for light profile microscopy (LPM) according to a still further embodiment of an apparatus according to the present invention.

DESCRIPTION OF EMBODIMENTS OF THE INVENTION

Figure 1:
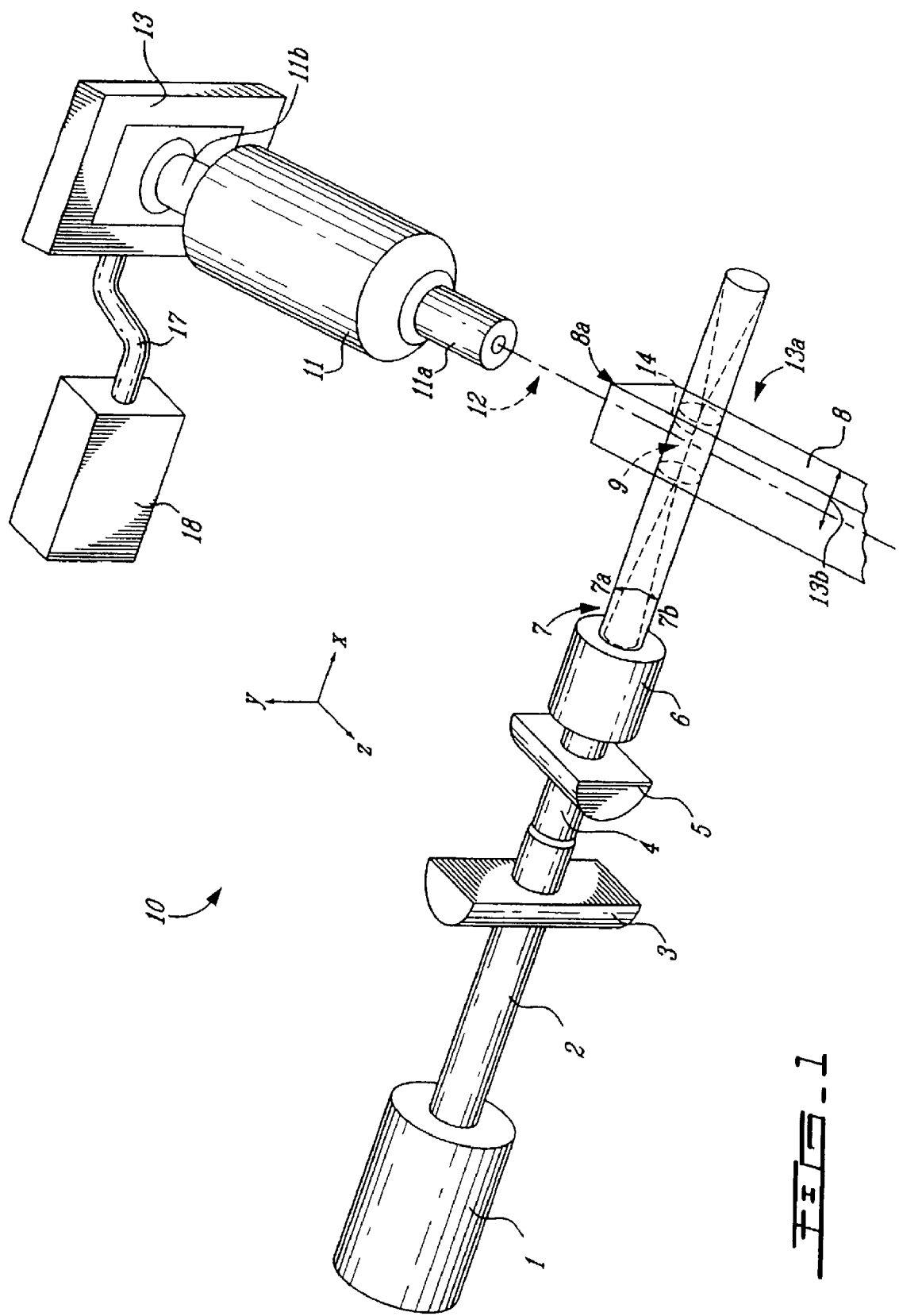
FIG. 1 is a schematic set-up for light profile microscopy (LPM) according to an embodiment of an apparatus according to the present invention.

Generally stated, there is provided a method and an apparatus for illuminating a sample in a light profile microscope (LPM) to obtain an optimized spatial resolution in a recorded image, under broad field conditions.

As will be explained further hereinbelow, image properties depend on a geometry of a source beam in the sample, including the size, shape, and alignment distance of the source beam behind an IT surface of the sample. This source beam geometry is in turn dictated by characteristics of the optical imaging system (OIS) used to form the LPM image.

As described hereinabove, the OIS used by a LPM comprises a combination of lenses and/or mirrors so arranged as to form an image of the sample in the LPM.

The OIS defines an object plane, and an image plane in which it forms an image of a system object consisting of a field of refracted or emitted light located in the OIS object plane. Each of the object plane and the image plane is oriented along transverse directions 'x' and 'y' and intersects an optic axis 'z'.

The OIS further defines a focal length, referred to as 'f', which is a fixed distance set by optical design, that relates the distance and location of the image relative to the system object according to a conjugate relationship as follows (see Warren J. Smith, Modern Optical Engineering, Second Edition, 1990, McGraw-Hill, New York):

$$\frac{1}{f} = \frac{1}{z_0} + \frac{1}{z_i} \quad (1)$$

where $z_0$ is an unsigned distance of the object plane from a first principal plane of the OIS, referred to as the object distance; and $z_i$ is an unsigned distance of the image plane from a second principal plane of the OIS, referred to as the image distance.

The image plane of the OIS is located in a fixed position. The image of a system object is formed in-focus at the image plane, in conformity to relation (1). An in-focus object is a system object, consisting of a field of emitted or refracted light of which the OIS forms an in-focus image at the image plane.

The system object of the OIS defines an object field, which is the set of all (x, y) points in the object plane from which light is admitted to the image plane unobstructed by the field stop of the OIS. The image of the OIS comprises an image field that is defined as the set of all (x,y) points in the image plane to which light is admitted from the object field unobstructed by the field stop of the OIS, and where each point of the image field and each point of the object field are related as follows:

$$x_i = M x_0 \quad (2a)$$

$$y_i = M y_0 \quad (2b)$$

where $x_i$ is the 'x' coordinate in image plane; $y_i$ is the 'y' coordinate in image plane; $x_0$ is the 'x' coordinate in object plane; $y_0$ is the 'y' coordinate in object plane; and M is the lateral magnification (a constant but signed quantity).

The OIS is a highly corrected optical system, wherein aberrations are corrected by design to a sufficiently low level that the image resolution is limited only by diffraction, and relations (1) and (2) apply at all points of the object and image fields, whereby residual aberrations do not contribute any significant effect on the image characteristics. In practice, a highly corrected OIS or a good approximation thereto, represents the target of an achievable optical system design. The OIS operates under a condition of fixed numerical aperture and magnification during the measurement of an image.

Although the OIS is assumed to be corrected to the diffraction limit, as is the standard with currently available optical designs, the present method may also use systems that are corrected only in an approximate sense. In these cases the minimum blur spot is aberration as opposed to diffraction limited, to within a maximum blur spot radius that is three times the diffraction limited value (see relation (6) hereinbelow). In these cases, the minimum blur spot is aberration limited as opposed to diffraction limited. Obviously, a similar but not identical set of criteria apply.

The present method allows a high image resolution from the OIS, as defined per a smallest spatial feature of which it may form an image. More specifically, the image resolution is here defined as the reciprocal of a minimum resolvable feature distance in the image formed by the OIS, which may be expressed as follows:

$$R = 1/(2\delta_r) \quad (3)$$

where $\delta_r$ is a minimum image feature radius (unsigned) resolvable by the OIS.

The smallest object feature of which the OIS may form an image is a point system object, which may be approximated, as optical theory teaches (see for example Warren J. Smith, Modern Optical Engineering, Second Edition, 1990, McGraw-Hill, New York.), in the case of an OIS that forms diffraction-limited images at fixed numerical aperture thereof and given wavelength $\lambda$, by a small, approximately spherical emitter located in the object plane of the OIS, with an average radius less than $\delta_{Ro}$ defined as follows:

$$\delta_{Ro} = \frac{0.61\lambda}{NA_o} \quad (4)$$

where $NA_o$ is the numerical aperture of the OIS on the object side.

The image of a point object located in or away from the OIS object plane is called a blur spot, while the image of a point system object is called a diffraction limited blur spot or an in-focus blur spot (see Warren J. Smith, Modern Optical Engineering, Second Edition, 1990, McGraw-Hill, New York.). Optical diffraction theory teaches that a diffraction limited blur spot corresponding to an on-axis point system object (located at x=y=0) has a radial intensity dependence $I_R(r)$ given by an Airy disc as follows (see Warren J. Smith, Modern Optical Engineering, Second Edition, 1990, McGraw-Hill, New York.):

$$I_R(r) = A_0 \left[ \frac{J_1(kNA_i r)}{(kNA_i r)} \right]^2 \quad (5)$$

where $I_R(r)$ is the (Airy disc) radial image intensity distribution; $A_0$ is a leading constant (with dimensions of intensity); k is the wave vector ($k=2\pi/\lambda$); $NA_i$ is the image side numerical aperture; and r is the radial distance from the optic axis $r=\sqrt{x^2+y^2}$. $J_1$ is the Bessel function of first order. The diffraction limited blur spot has a radius $\delta_{Ri}$ as follows:

$$\delta_{Ri} = \frac{0.61\lambda}{NA_i} \quad (6)$$

For an on-axis point object displaced from the object plane of the OIS by a small axial distance $\Delta z_0$, referred to as the axial defocus offset distance, the blur spot has a radius larger than the minimum value given by relation (6). The condition $\Delta z_0 \neq 0$ corresponds to a condition of defocus of the point object. The larger the magnitude of the axial defocus offset distance $\Delta_{z0}$ of the on-axis point object, the larger the effective radius of the blur spot that forms in the image plane. Optical diffraction theory teaches that the blur spot formed of an on-axis (x=y=0) point object that is displaced at the axial defocus offset distance $\Delta z_0$ from the object plane, and has an intensity as follows (see J. F. Power, Fresnel Diffraction Model for the Point Spread of a Laser Light Profile Microscope, *Applied Physics B* 78, 693-703 (2004)):

$$h(r, z) == \frac{A_0}{\xi^2} [L_1^2(\xi, \eta) + L_2^2(\xi, \eta)] \quad (7)$$

where $A_0$ is a leading constant (with dimensions of intensity);

$$\xi = \frac{\pi}{2} \cdot \frac{\Delta z_0}{\delta_0}$$

is a defocus variable, expressed in terms of the object defocus $\Delta z_0$; and the object depth of focus $\delta_0$ (as defined below in relation (8)); $\eta = k NA_i r$ is the transverse variable expressed in terms of the wave number k, the image side numerical aperture $NA_i$ and the radial variable $r=\sqrt{x^2+y^2}$; and $L_1(\xi, \eta)$ and $L_2(\xi, \eta)$ are the Lommel functions, defined as:

$$L_1(\xi, \eta) = \sum_{n=0}^{\infty} (-1)^n \left(\frac{\xi}{\eta}\right)^{2n+1} J_{2n+1}(\eta)$$

and $$L_2(\xi, \eta) = \sum_{n=0}^{\infty} (-1)^n \left(\frac{\xi}{\eta}\right)^{2n+2} J_{2n+2}(\eta)$$

where $J_m(\eta)$ are Bessel functions of order m.

The radial dependence of the blur spot in relation (7) reduces to the Airy disk (relation (5) as $\Delta z_0$ approaches zero). Because the OIS is a highly corrected optical system, the dependence of the blur spot intensity on the radial distance from the blur spot center shows no variation for off axis field points having non-zero (x, y) central position in the object or image field.

Optical theory (see for example Warren J. Smith, Modern Optical Engineering, Second Edition, 1990, McGraw-Hill, New York; J. F. Power, Fresnel Diffraction Model for the Point Spread of a Laser Light Profile Microscope, *Applied*

*Physics B* 78, 693-703 (2004)) further teaches that, for an OIS operating at fixed wavelength and aperture, there is a maximum axial defocus offset distance of a point object from the object plane, referred to herein as the object depth of focus of the OIS $\delta_0$, such that there is no significant difference in the blur spot radius from the diffraction limited value of relation (6), defined as follows:

$$\delta_0 = \frac{\lambda}{4NA_0^2} \quad (8)$$

where $\lambda$ is the wavelength of the image light, and $NA_0$ is the numerical aperture of the OIS on the object side.

Object point sources lying within one object depth of focus of the object plane of the OIS produce a set of blur spots that are not significantly defocused and that closely approximate the diffraction limited blur spot of relation (5). A thin object, defined as an object having all points of its field confined to within a 'z' axial interval of length $\pm\delta_0$ with respect to the object plane position, forms an image that gives a good approximation to the in-focus condition. The minimum resolvable feature distance in the image for all (x, y) field points of a thin object is then at the diffraction limit, per relation (3) with $\delta_r = \delta_{Ri}$.

Taking into account the fact that, in the general set up of a LPM, the object imaged by the OIS is not necessarily thin, the present method provides that the object imaged in the LPM makes either a good approximation to, or a controlled departure from, the thin object condition. This ensures a high resolution in the OIS image, which, as measured by the blur spot radius, is either at the diffraction limit or within specified close limits thereof.

More specifically, the present method establishes the object in the LPM, referred to as the LPM object, in the test material by the intersection of the source beam with the test material. This intersection defines an irradiated volume of the test material, from which light is emitted by several possible mechanisms, including elastic scatter, inelastic scatter, luminescence and/or blackbody emission. The LPM object is a three dimensional spatial distribution of light thus emitted in the irradiated volume, where the distribution of emitted light is linearly proportional to the local (x, y, z) intensity of the source beam.

Standardly in the prior art, the source beam is a cylindrical Gaussian TEM (0,0) laser beam, propagating along the depth direction 'x', for which the profile of source beam intensity in the test material is defined per relation (9) as follows:

$$I_s(x, y, z) = \frac{I_0}{\pi \omega^2} \exp[-2(y^2 + (z - z_s)^2)/\omega^2] \quad (9)$$

where $I_s$ (x, y, z) is the spatial dependence of the Gaussian laser beam's irradiance; $\omega$ is the mode field radius (beam spot size) along 'x' in the xy and xz planes; $I_0$ is a leading constant with dimensions of an intensity; and $z_s$ the center of excitation beam along the 'z' axis behind the IT surface (measured from the IT surface). The Gaussian beam radius so relates to the radial distance from the beam center at which the Gaussian intensity profile is attenuated to a value of $e^{-1}$ of the value at the beam center, therefore defining an effective radius for the source beam.

Also standardly in the prior art, the source beam is collimated to form a beam waist in the test material, centrally aligned at the center of the object field (at x=y=z=0), a laser beam waist being defined in Gaussian beam theory as the axial position of the beam at which the beam radius has a minimum value $\omega = \omega_0$. A region of approximate collimation, referred to as the Rayleigh range, is symmetrically distributed along 'x' with respect to the waist position. The width of the Rayleigh range is given from theory per the following:

$$X_C = \frac{\pi \omega_0^2}{\lambda_s} \quad (10a)$$

where $X_C$ is the confocal distance of the Gaussian beam; $\omega_0$ is the mode field radius (beam spot size) at the waist position; and $\lambda_s$ is source beam wavelength; and:

$$X_R = 2 X_C \quad (10b)$$

where $X_R$ is the width of the Rayleigh range.

Inside the Rayleigh range, the laser beam radius deviates from the value $\omega_0$ by no more than the maximum value $\omega_0\sqrt{2}$.

As in the prior art already mentioned, in the present method, the width of the object field along the axis 'x' is less than or equal to the width of the Rayleigh range of the source beam in the sample. The source beam waist is normally aligned in the test material to coincide with the central optic axis of the microscope. The source beam 'x' axis is aligned at or within a distance along 'z' of $\pm 2\delta_0$ of the object plane of the OIS.

The effective 'z' axial width of the LPM object is thus set by the radius of the source beam. When the radius of the source beam is maintained smaller than the object depth of focus of the OIS, then $\omega_0 < \delta_0$ and the thin object condition is valid for the LPM object. All points of the LPM object are then in-focus. In this case the minimum resolvable feature distance in the LPM image is a close approximate to the minimum value limited by diffraction, for a point system object, relation (6) and the resolution is the maximum possible limited by diffraction.

For a number of practical cases of LPM, a compression of the source beam radius, required to achieve the condition $\omega_0 < \delta_0$, results in a very narrow cylindrical irradiated volume in the test material. The LPM object then has the form of a narrow radius cylinder oriented along the depth axis. The field of excitation of the test material along the vertical 'y' dimension is then very restricted and an accordingly limited vertical image of the object along the 'y' dimension is obtained. The resulting LPM image then reduces to a line image deprived of vertical information about the object. Excitation with a line image does have certain advantages as cited in the art (see U.S. Pat. No. 6,614,532 for example), as when the LPM image is coupled through a spectrograph to provide a wavelength resolved line profile image. However, in the most general cases, inspection with a line source is restrictive, and correction of this restriction is desirable.

The present method allows correcting this limitation by exciting the test material with an elliptical source beam that approximates a thin plane sheet of excitation oriented in the (x, y) plane with a thinnest dimension thereof along the optic axis 'z' and a major dimension along the 'y' direction. Such a beam may be produced by an optical system such as an anamorphic collimator. The anamorphic collimator consists of a combination of optical components, including lenses or mirrors, some of which are cylindrical or toroidal optical elements (as known in the art, see for example Warren J. Smith, Modern Optical Engineering, Second Edition, 1990, McGraw-Hill, New York, pp. 270-278), which independently collimate an incoming cylindrical beam along two orthogonal axes.

The axis of propagation of the elliptical source beam in the LPM is oriented along 'x' in the test material. The elliptic source beam has an elliptical intensity variation in the (y, z) plane, with a major elliptic axis of the variation oriented along the vertical direction 'y' and the minor elliptical axis oriented along the optic axis 'z'.

The beam entering the elliptic collimator may be a Gaussian TEM (0,0) laser beam, resulting in a output beam produced by the collimator having the form of an elliptic Gaussian beam, with a transverse intensity profile as follows:

$$I_{sE}(x, y, z) = \frac{I_0}{\pi(\omega_y, \omega_z)} \cdot \exp[-2(y^2/\omega_y^2) + (z-z_s)^2)/\omega_z^2] \quad (11)$$

where $I_{sE}(x, y, z)$ is the spatial dependence of the elliptically collimated source beam's irradiance; $\omega_y$ is the mode field radius (beam spot size) in the xy plane; $\omega_z$ is the mode field radius (beam spot size) in the xz plane; $I_0$ is a leading constant with dimensions of an intensity; $z_s$ is a center of excitation beam along the 'z' axis behind the IT surface (distance measured from the IT surface).

Such a beam may be controlled to have a unique waist position along the propagation 'x' axis, at which the beam radii simultaneously have the minimum values $\omega_y=\omega_{0y}$ and $\omega_z=\omega_{0z}$ along the axes 'y' and 'z'. The beam also have two orthogonally oriented Rayleigh ranges that are applicable along axes 'y' and 'z' per relations (10a) and (10b), with $\omega_0=\omega_{0y}$ and $\omega_0=\omega_{0z}$, to give $X_{Cy}, X_{Ry}$ and $X_{Cz}, X_{Rz}$ respectively, centered at the waists. Finally, the elliptic source beam is centered in the test material at the center of the depth 'x' field, at which the optic axis of the OIS intersects the 'x' axis.

The beam illumination provided by an elliptic laser beam according to an embodiment of the method of the present invention approximates a plane sheet oriented in the (x, y) plane and centered at the object plane of the OIS. The extent of the 'xy' field of the beam imaged by the OIS is large and rectangular or square, with dimensions that are large relative to the beam thickness along 'z'. Because of the small 'z' axial thickness, a high and controlled LPM image resolution is obtained. Furthermore, a high concentration of image light is achieved within the narrow 'z' axial range, ensuring high image brightness, with a large fraction of light in the object imaged in focus.

There are practical limits on the usable 'z' axial thinness of the elliptic beam. These arise because the width of the region of collimation of the laser beam (the Rayleigh range, relations (10a) and (10b)) becomes narrower as $\omega_{0z}$, at the beam waist radius, becomes sufficiently small. This places restrictions on the minimum 'z' axial radius of the source beam, for certain cases, such as when the OIS operates at large magnification and aperture. These restrictions are discussed in detail hereinbelow.

The controlled 'z' axial thickness of the elliptic source beam allows a control of the minimum resolvable feature distance and thus image resolution in the LPM image. The extent to which the 'z' axial thickness of the LPM object affects the image resolution of the LPM image may be quantitatively assessed with reference to theory (see for example J. F. Power, Fresnel Diffraction Model for the Point Spread of a Laser Light Profile Microscope, *Applied Physics B* 78, 693-703 (2004)). The resolution of a LPM image is defined per relation (3). The minimum resolvable feature distance $\delta_r$ is the radius of the blur spot formed by the LPM, denoted $\delta_{LPM}$. The LPM blur spot is the image formed by the OIS of a single field point of the LPM object. The LPM object field is defined as the set of all (x, y) points of the irradiated volume from which light is admitted to the image plane unobstructed by the field stop of the OIS.

Each field point of the LPM object field has an axial depth or distance along 'z'. It has been recently shown in the art (see J. F. Power, Fresnel Diffraction Model for the Point Spread of a Laser Light Profile Microscope, *Applied Physics B* 78, 693-703 (2004)), that, at fixed (x, y) field in the LPM object, the LPM blur spot forms as the integral (sum) of a set of weighted blur spots originating from all source points distributed continuously along 'z' in the LPM object volume. At fixed (x, y), each 'z' axial point in the object volume contributes an individual blur spot, which is proportionally weighted by the local value of the emitted source beam intensity $I_s(x, y, z)$. A suitable test material has optical properties that vary slowly in the 'z' direction, meaning that they do not vary significantly within a distance of $\pm 10\ \delta_0$ to ensure the validity of relation 11. The image that appears in the image plane of a single field point of the LPM object is the summation (superposition) of these weighted blur spots, as described from theory as follows:

$$h_L(r) = \frac{\Phi I_0}{\pi \omega_0^2} \int_0^z \exp[-(2(z-z_s)^2/\omega_0^2]h(r, z-z_0')dz \quad (12)$$

where $h_L(r)$ is the point spread function for the LPM excited with a conventional cylindrical beam; $\phi$ is the efficiency of scatter or luminescence from the object volume (constant over the volume); $I_0$ is the integral beam intensity (constant); $\omega_0$ is the mode field radius (beam spot size) of the source beam; $z_s$ is the distance of the source beam from the IT surface; h(r, z) is a point spread function of the objective lens (having dependence as given in relation (7) hereinabove); $z_0'$ is the distance of the object plane from the IT surface; and z is a distance along the optic axis.

The superposition property of axial blur spots described by relation (12) results in that a narrow source beam, with radius $\omega_0$ close in value to $\delta_0$, concentrates more light close to the object plane, and produces an LPM blur spot that approximates the Airy disc or diffraction limited blur spot of relation (5). The result is a sharp image with a best possible resolution limited by diffraction. A wider source beam radius includes more out-of-focus light in the object volume, and produces a more diffuse blur spot, with contributions originating from object points significantly displaced away from the object plane, resulting in a more defocused, less resolved image.

Diffraction theory enables the calculation of an effective blur spot radius for the case of an LPM image where the source beam is cylindrical, coo is specified, and the numerical aperture, magnification and imaging wavelength of the OIS are known (see J. F. Power, Fresnel Diffraction Model for the Point Spread of a Laser Light Profile Microscope, *Applied Physics B* 78, 693-703 (2004)). The LPM blur spot radius is defined as follows:

$$\frac{\int_0^{\delta_{LPM}} h_L(r)dr}{\int_0^\infty h_L(r)dr} = 0.975 \quad (13)$$

where $\delta_{LPM}$ is the LPM blur spot radius and $h_L(r)$ is the LPM point spread function (see relation (12)). From relation 13, $\delta_{LPM}$ may be determined graphically as a radial interval that brackets 97.5% of the one-dimensional radial integral of $h_L(r)$.

Table 1 summarizes the relative minimum resolvable feature distance available from a LPM image in terms of the relative object thickness. The minimum resolvable feature distance for the LPM image is defined as twice the radius of the LPM blur spot $\delta_{LPM}$. The relative minimum resolvable feature distance available from the LPM image is expressed as the ratio $\delta_{LPM}/\delta_{Ri}$, which measures the LPM minimum resolvable feature distance in multiples of the diffraction limited value from relation (6). The relative object thickness is measured as the ratio $\omega_0/2^{1/2}\delta_0$, which expresses the source beam radius in multiples of the OIS object depth of focus. These data (see J. F. Power, Fresnel Diffraction Model for the Point Spread of a Laser Light Profile Microscope, *Applied Physics B* 78, 693-703 (2004)) apply at fixed imaging wavelength over a wide range of spot radius values $\omega_0$ in the range comprised between 0.5 and 500 μm, and over a full range of magnification and numerical aperture of the OIS.

TABLE 1

| $\omega_0/2^{1/2}\delta_0$ | $\delta_{LPM}/\delta_{Ri}$ |
|---|---|
| 0.54 | 1.12 |
| 2.72 | 1.40 |
| 5.44 | 1.96 |
| 13.68 | 3.22 |
| 19.12 | 3.57 |
| 27.28 | 3.78 |

Conditions that are found to ensure a high resolution in the LPM image over a known image field along the depth axis will now be presented.

Diffraction theory and the results of Table 1 indicate that when the 'z' axial beam dimension $\omega_{0z}$ is less than five times the object depth of focus $\delta_0$, the minimum resolvable feature distance in the LPM image is no more than twice the Rayleigh limited blur spot radius $S_{Ri}$. If this condition is maintained in the LPM beam illumination, then a high resolution, corresponding to one half the maximum possible value for the OIS, is obtained in the LPM image. However, as $\omega_{0z}$ decreases, the Rayleigh range in the (x, z) plane diminishes in length per relations 10a and 10b with $X_C = X_{Cz}$ and $\omega_0 = \omega_{0z}$. Because the beam radius $\omega_{0z}$ is controlled to a nearly constant value only within the 'x' axial width of the Rayleigh range, the 'x' field width of the LPM image for which high image resolution is obtained, is, under illumination with an elliptical beam, set by the width of the Rayleigh range. This 'x' field width may also be measured in units of theoretical image pixels, where the theoretical pixel width is the minimum resolvable feature width $\Delta X_{LPM}$, as follows:

$$\Delta X_{LPM} = \frac{X_{Cz}}{\delta_{LPM}} \quad (14)$$

where $\Delta X_{LPM}$ is the size of 'x' field of the LPM (as number of resolvable pixels); $X_{Cz}$ is the confocal distance of the source beam in the xz plane per relation (10a) hereinabove with $\omega_0 = \omega_{0z}$; and $\delta_{LPM}$ is the minimum spot radius resolvable by the LPM.

Under illumination with an elliptical beam, the width of the field in the LPM along 'y', for which high image resolution is obtained, is set by the beam radius $\omega_{0y}$, which may be adjusted to an arbitrarily large value, although a radius of 10-100 X the $\omega_{0z}$ value may be typical. The extent of the 'y' field may be adjusted to yield a desired light concentration in the LPM object, given an area to be illuminated in a test material.

Even when $\omega_0 > 5\delta_0$, planar illumination may still provide a benefit to a LPM. As Table 1 shows, when the object dept of focus is up to 25 times smaller than the source beam radius, i.e. when $\omega_0 > 25\delta_0$, $\delta_R$ approaches $4\delta_{Ri}$, which means that the resolution is still acceptable. Optical theory teaches that in this situation, spatial resolution is controlled by an object focus envelope that acts to suppress out-of-focus light. Planar illumination provides a large area as described hereinabove for sample inspection with enhanced concentration of light into the illuminated volume (over the case of conventional excitation with a cylindrical beam), which may be of interest in practical situations.

A LPM with elliptical illumination may be characterized as operating under two regimes, referred to respectively as Regime 1 and Regime 2.

Assuming that the OIS operates at a visible wavelength, Regime 1 applies approximately at low-to-moderate numerical aperture (object side, $NA_O$) and magnification (M) of the OIS, where $NA_O \leq 0.4$ and $M \leq 20 \times$ approximately, according to the Royal Microscopical Society (RMS) standard, or other microscopy standard systems (DIN and JIS), which numerically approximate the RMS standard.

Regime 2 applies approximately for numerical aperture and magnification values above the limits specified by Regime 1.

In Regime 1, the size of the 'x' axial field is large: $\omega_{0z}$ may be maintained within the limit $\omega_{0z} < 2\delta_0$ while maintaining an 'x' axial field at least 10 theoretical pixels wide, per relation (14).

In Regime 2, $\omega_{0z}$ is maintained at small values that restrict the 'x' axial field of the LPM image to below 10 theoretical pixels in width. In this case, the field of the LPM image with high image resolution is approximated by a thin strip vertically oriented along the 'y' direction. The restricted with of the 'x' axial field in this case may not alter the high resolution of two dimensional LPM image, providing modification of the apparatus is introduced. A high resolution two dimensional LPM image of wide 'x' field may still be recovered under elliptic illumination, providing a series of LPM strip images is acquired with step scanning at a set of field positions along 'x' that are spaced by the field width $\Delta X_{LPM}$. This produces a series of contiguous high-resolution LPM images that may be pieced together after acquisition of the image series.

In addition to the above-identified conditions, the method of the present invention allows for a number of alternative arrangements, as will now be described.

It is found that the spatial coherence of the source beam is not essential. While a laser may be used, a broadband radiation source equipped with suitable elliptical collimation optics may also be used. In the case of collimation systems used by broadband sources, the region of beam collimation is not specifically described by a Rayleigh range as defined in relations (10a) and (10b), but by beam collimation criteria specific to the individual collimator's optical design. Incoherence of the image radiation may not be essential, but there may be losses in image resolution in cases where the image radiation is partially or fully coherent. Monochromaticity of the source radiation may not be essential, although it may often desirable in many applications. Monochromaticity of the image radiation may not be essential, although different specifications of beam radius, image resolution, object depth of focus and length of source beam collimation region apply at the different wavelengths imaged, which is to be taken into account.

The method according to the present invention operates over the ultraviolet (200 nm) through to the near infrared (1000 nm) wavelength range. The invention may further have applicability to operation with X-rays and electron beams, provided suitable collimation and imaging optics are available. The method comprises alignment of the source beam's central axis in the object plane of the OIS, and may allow an alignment tolerance of the beam's central axis to within $\pm 8\delta_0$ of the OIS object plane, in some cases, with a possible loss of image resolution.

The method of the present invention, may further allow relaxing a requirement for a substantial parallelism between the IT surface and the 'x' axis of the elliptically collimated beam. In this case, the elliptically collimated source beam may be directed to enter the test material through the IT surface at an angle to the surface normal comprised between zero and ninety degrees. An irradiated volume is formed from the intersection of the source beam and the test material. This irradiated volume then has a planar structure resulting from irradiation with an elliptically collimated beam. The OIS may be aligned along an optic axis so as to image the irradiated volume in the test material along the 'x' axis as specified."

Turning to the FIGS. 1-4 of the appended drawings, embodiments of an apparatus according to the present invention will now be described.

FIG. 1 schematically shows a light profile microscope apparatus according to an embodiment of the invention, which comprises a radiation source 1 supplying a source beam 2.

The radiation source 1 may be a laser supplying a Gaussian TEM (0,0) beam and radiation with an output wavelength in the range from the quartz ultraviolet through to the long wavelength near infrared. Infrared radiation may be contemplated, although in this wavelength range the image resolution of infrared optical systems may be a limitation. X-ray sources may also be used, as discussed hereinabove. The source radiation may be monochromatic or a modified white light source as discussed herein below.

The source beam 2 may be approximately collimated by being propagated through an anamorphic collimator, which is shown in FIG. 1 as the combination of elements 3, 5 and 6. The anamorphic collimator forms an elliptically collimated source beam 7 with major and minor elliptic axes 7a and 7b along axes 'y' and 'z' respectively.

In this example, the anamorphic collimator comprises two orthogonally oriented cylindrical lenses 3 and 5, respectively oriented along the 'y', and 'z' axis. The cylindrical lens 3 focuses the incoming beam 2 in the xz plane, while the cylindrical lens 5 focuses a beam 4 emerging from the cylindrical lens 3 in the yz plane. The relay lens system 6 forms the beam 7, which maintains collimation over an axial collimation (Rayleigh) regions in the xz plane and in the yz plane. The focal lengths of the lenses 3 and 5 are selected to independently adjust radial widths along 'z' and along 'y' of the beam 7 to yield a radial width $\omega_{0y}$ along the major axis 7A and a radial width $\omega_{0z}$ along the minor axis 7B of the elliptical beam 7.

In the case when the source beam 2 is a Gaussian laser beam, the elliptic source beam 7 formed by the anamorphic collimator 3, 5, 6 has a beam waist 14, which is the x axial position of minimum beam radius along both y and z dimensions $\omega_{0y}$ and $\omega_{0z}$. The regions of collimation of the elliptic source beam are the Rayleigh ranges of the Gaussian beam 7 in the xz and xy planes, thereby centered at the waist position 14. The beam waist of the elliptic source beam formed by the anamorphic collimator 3, 5, 6 is normally centered inside a test material 8, and the region of axial collimation of the elliptic beam is normally of much longer dimension than the 'x' axial thickness of the test material 8 to be probed.

The beam width $\omega_{0z}$, of the elliptical source beam 7 along the 'z' direction is adjusted so that $\omega_{0z}$ is less than five times the object depth of focus $\delta_0$ (relation (8)) of an optical imaging system 11. The beam width $\omega_{0y}$ is normally set to a value at least ten times that of $\omega_{0z}$ to provide an object field along 'y'. The elliptically collimated source beam 7 intersects the test material 8 to form an irradiated volume 9 therein, in such a way that the region of axial collimation of the source beam is normally centered near the center of the test material along the axis 'x'. The elliptical beam 7 in the illuminated volume 9 has effective radial width dimensions $\omega_{0z}$ and $\omega_{0y}$. The elliptically collimated source beam 7 is aligned adjacent to an image transfer (IT) surface 8a oriented substantially parallel to the major axis 7a of the beam 7. A radiation scattered or emitted from the irradiated volume 9 of the test material 8 is collected by the aperture of an optical imaging system (OIS) 11. The optic axis 12 of the OIS 11 is aligned substantially along the direction 'z' and the OIS object plane is aligned at or in proximity to the central 'x' axis of the irradiated volume 9 in the test material 8.

In this embodiment the OIS 11 further comprises an objective lens 11a and a tube lens 11b, which form an image of the irradiated volume 9 at a camera 13 aligned in the image plane of the OIS 11. The output of the camera 13 is transmitted to a storage electronics resident computer or digital image storage system 18, via an interface cable 17, for example.

The apparatus 10 illustrated in FIG. 1 operates in Regime 1 discussed hereinabove.

Figure 2:
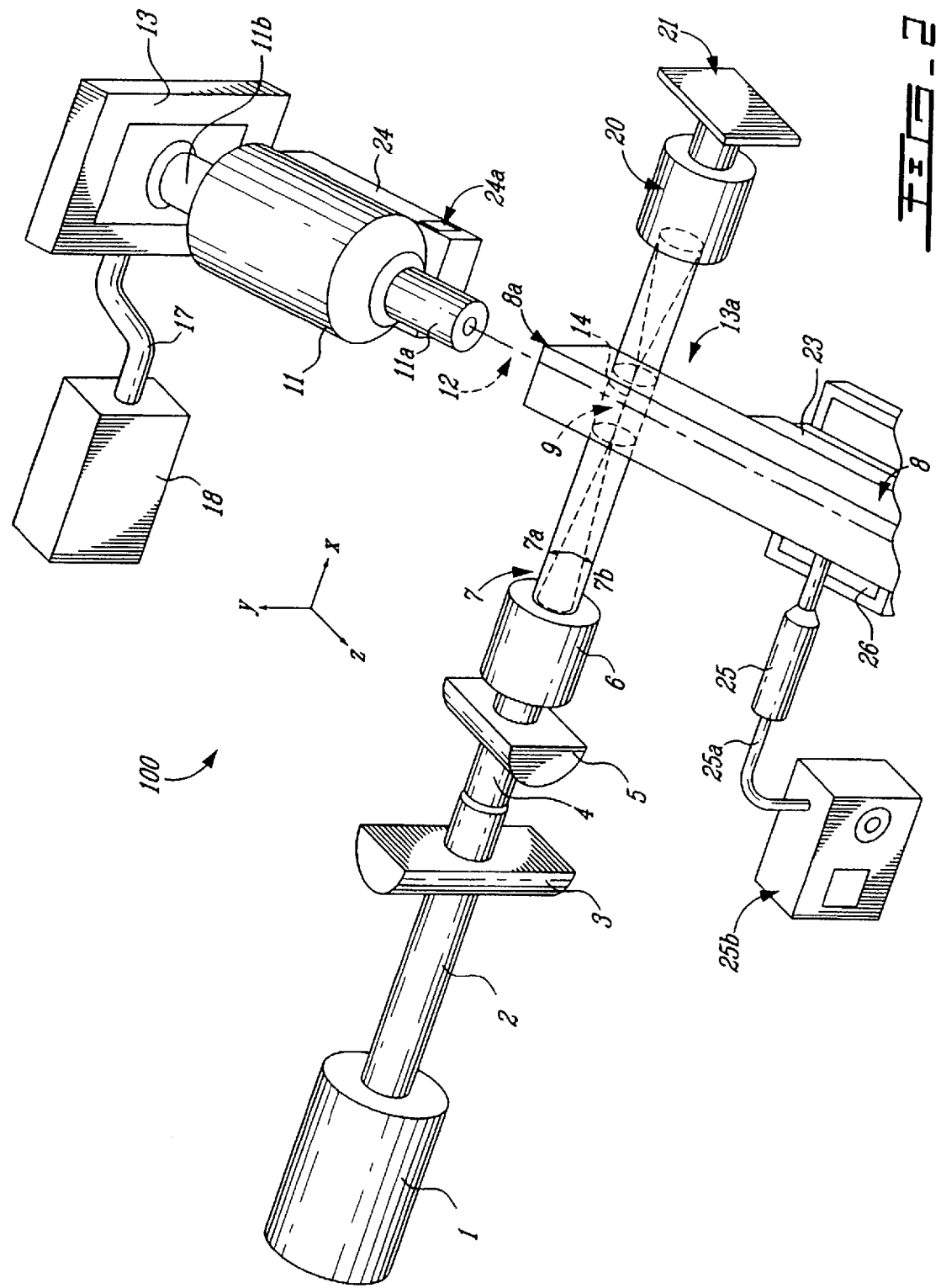
FIG. 2 is a schematic set-up for light profile microscopy (LPM) according to another embodiment of an apparatus according to the present invention.

FIG. 2 illustrates another embodiment of the apparatus of the invention, which operates in Regimes 1 and 2 discussed hereinabove.

The apparatus 100 comprises a number of elements with similar component functions to identically numbered elements in the apparatus 10 of FIG. 1, as well as a number of additional elements.

The apparatus 100 comprises means, including an imaging lens assembly 20 and alignment camera 21, for aligning the source beam in the test material 8 at a known position behind the IT surface 8a, whereby the imaging lens assembly 20 forms an image of the test material at the alignment camera 21. Furthermore, the test material 8 is provided with a micro-translation stage 23, which enables the center of the elliptical beam in the test material 8 to be set at a known z-axial distance behind the IT surface 8a. Therefore, in apparatus 100, the approximate structure of the source beam in the test material 8 is that of a thin plane, which samples a desired (x, y) region of the sample at a known axial distance 'z' behind the IT surface 8a. This sampling arrangement functions analogously to an optical microtome.

The optical imaging system (OIS) 11 further comprises a micro-translation stage 24 including a readout 24a, which allows the position of the object plane of the OIS in the test material 8 to be accurately established.

A stepper motor 25, which precisely drives a translation stage 26 with sub-micrometer accuracy, enables operation of the apparatus 100 in Regime 2. A motor controller 25b communicating with the stepper motor 25 via a cable connector 25a drives the stepper motor 25. The stepper motor 25 enables a series of contiguously spaced images to be recorded along the 'x' field, where each image has a full 'y' field at each point along 'x'. These images are read by the camera 13 and stored by the system 18 that uses computer software to assemble a full 'xy' field image of the sample from the individually recorded images.

Figure 3:
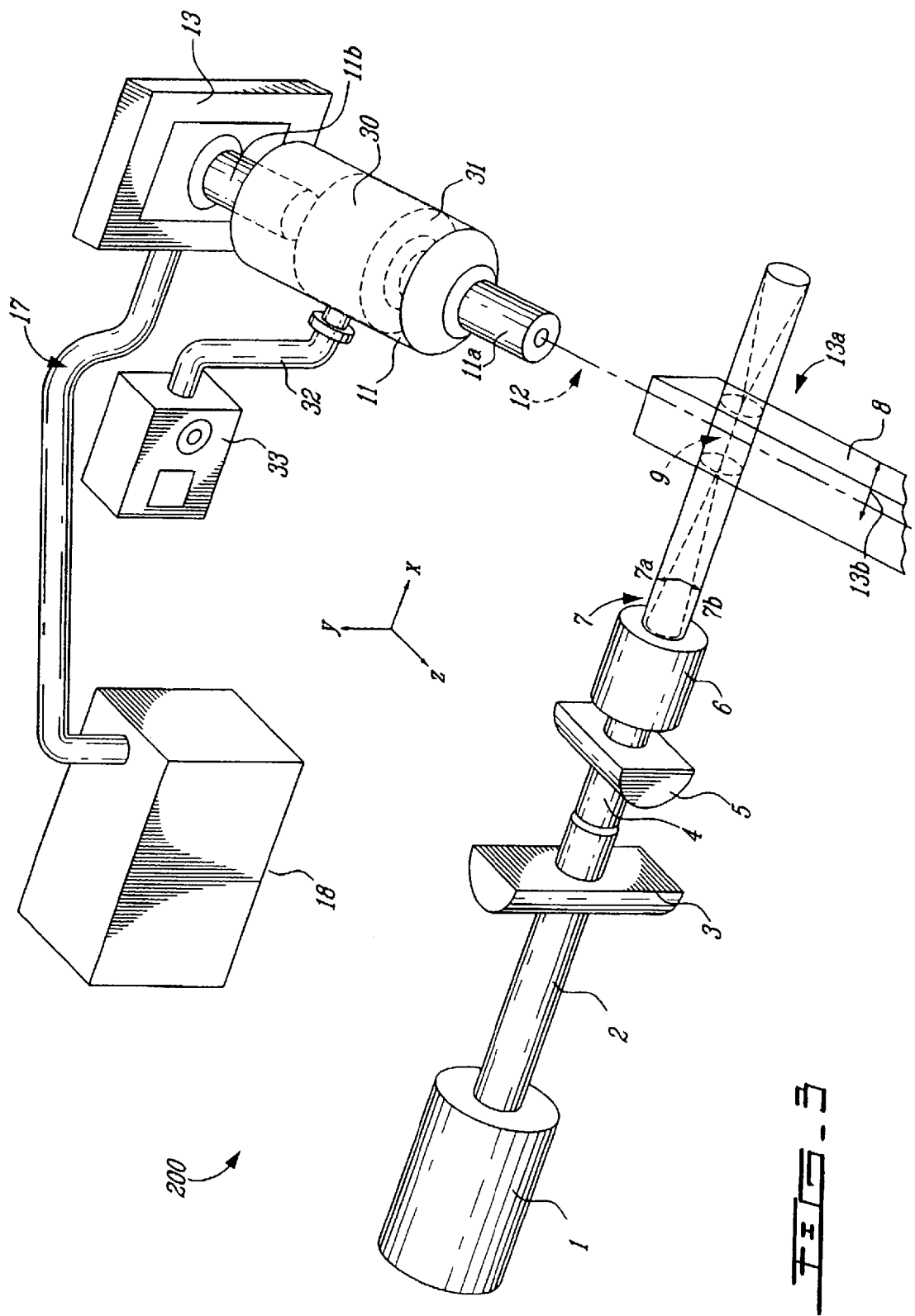
FIG. 3 is a schematic set-up for light profile microscopy (LPM) according to a further embodiment of an apparatus according to the present invention.

FIG. 3 illustrates a further embodiment of the apparatus of the present invention.

This apparatus 200 comprises elements that form a combination of elements with similar component functions to identically numbered elements of the apparatus 10 of FIG. 1.

Apparatus 200 further comprises means for enabling the image to be formed over a narrow band of wavelengths. A liquid crystal tunable filter (LCTF) 30, by filtering the radiation processed by the objective lens 11a of the OIS over a narrow band of wavelengths, typically with a bandwidth of less than 1 nm, allows wavelength resolution, the objective lens 11a being correspondingly set to have its focus corrected at infinity (i.e. it is a so-called infinity corrected objective). An order-sorting filter 31, placed ahead of the LCTF 30, selects first order radiation therefrom. The LCTF 30 receives operating voltages from a system of control electronics 33, through a cable interface 32. Under operation, the LCTF 30 operating voltages are scanned to continuously vary the central wavelength of the LCTF element.

Apparatus 200 allows recording of wavelength resolved images.

The embodiment illustrated in FIG. 4 relates to a case of an absence of a substantial parallelism between the IT surface and the 'x' axis of propagation of the elliptically collimated beam. This allows the invention to be implemented for imaging of the irradiation volume without the requirement for obtaining or preparing a cross sectional edge of the material.

The source laser beam 2 from the source laser 1 is directed through the anamorphic collimator 3 to give the elliptically collimated beam 7 that is directed into the test material 8, entering through the IT surface 8a. The intersection of the elliptically collimated beam 7 with the test material 8 results in the irradiated volume 9. An OIS 11 is aligned along an optic axis 12, which need not be substantially orthogonal to the 'x' axis but which is shown as such in FIG. 4. The OIS is equipped with objective 11a and tube 11b lenses that form an image of the irradiated volume 9 at the camera 13 aligned in the OIS image plane. The output of the camera 13 is transmitted to the storage electronic system 18 via the interface cable 17.

Although the present invention has been described hereinabove by way of embodiments thereof, it may be modified, without departing from the nature and teachings of the subject invention as describes herein.

What is claimed is:

1. An apparatus for illuminating a test material in a light profile microscope, comprising:
a source of radiation providing a source beam propagating along a beam axis x;
an anamorphic optical means providing, from the source beam emitted by said source of radiation, a source beam elliptically collimated over an x axial collimation region having a distance comprised in a range between micrometers and meters, and having a major elliptic axis oriented along a first transverse axis y, and a minor elliptic oriented along a second transverse axis z;
a test material positioned to intersect the elliptically collimated source beam within the x axial collimation region to form an irradiated volume, said test material comprising an image transfer surface oriented substantially parallel to the x axis and substantially orthogonal to the z axis, said image transfer surface transmitting radiation emitted from said irradiated volume in said test material;
an optical imaging system forming an image, at an image plane, of the illuminated volume in the test material from the radiation transmitted by the image transfer surface; said optical imaging system defining an object plane conjugate to the image plane and aligned to contain the major elliptic axis of the collimated source beam intersecting said test material in the illuminated volume, an object depth of focus of said optical imaging system being maintained at a value of approximately at least ⅕ of a radius of the elliptically collimated source beam along the z axis in the axial collimation region of the elliptically collimated source beam; and
image receiving means receiving the image formed by said optical imaging system in the image plane thereof;
wherein said apparatus yields a high image resolution and wide image field.

2. The apparatus according to claim 1, wherein said anamorphic optical means includes ones of cylindrical and toroidal optical elements that independently collimate the source beam along orthogonal axes y and z transverse to the beam propagation axis x.

3. The apparatus according to claim 1, wherein the image transfer surface transmits radiation emitted one of scattering, luminescence and blackbody emission from the irradiated volume in the test material.

4. The apparatus according to claim 1, wherein said optical imaging system comprises at least one of lenses, mirrors and a combination thereof.

5. The apparatus according to claim 1, wherein said image receiving means comprises means for at least one of recording, displaying, storing and a combination thereof.

6. The apparatus according to claim 1, wherein said source of radiation is a laser, said anamorphic optical means is an anamorphic collimator comprising a combination of at least ones of cylindrical lenses and mirrors, the irradiated volume of the test material emits luminescence, and said image receiving means is a high sensitivity CCD camera.

7. The apparatus according to claim 6, wherein said test material emits elastic scatter from the irradiated volume.

8. The apparatus according to claim 6, wherein said test material emits Raman scatter from the irradiated volume and said optical imaging system further comprises an optical filter that selects a narrow range of emitted wavelengths to form the image at the CCD camera.

9. The apparatus according to claim 6, wherein said test material emits luminescence from the irradiated volume and said optical imaging system further comprises an optical filter that selects a narrow range of emitted wavelengths to form the image at the CCD camera, 10. The apparatus according to claim 6, wherein said laser is a high intensity laser that thermally excites the test material's irradiated volume causing chemiluminescence to be emitted from the irradiated volume.

11. The apparatus according to claim 1, wherein said source of radiation is a broadband radiation source emitting polychromatic radiation, said anamorphic optical means is an anamorphic collimator comprising one of a combination of cylindrical lenses and a combination of anamorphic mirrors, the irradiated volume of said test material emits elastic scatter, and said image receiving means is a CCD camera.

12. The apparatus according to claim 1, wherein the object depth of focus of said optical imaging system is maintained at a value comprised between 1/5 and 5 times the radius of the elliptically collimated source beam along the z axis in the axial collimation region of the elliptically collimated source beam.

13. A method for illuminating a test material in a light profile microscope comprising a source of radiation, an anamorphic collimator, an optical imaging system and an image recording means, said method comprising the steps of:
   propagating a source beam emitted by the source of radiation along a beam propagation axis x;
   elliptically collimating the source beam along orthogonal axes y and z transverse to the beam propagation axis x to yield a elliptically collimate source beam over an x axial collimation region having a distance comprised in a range between microns and meters, and having a major elliptic axis oriented along the transverse axis y and a minor elliptic oriented along the transverse axis z;
   intersecting the elliptically collimated source beam 'within the x axial collimation region with a test material to form an irradiated volume in the test material by said intersecting, and aligning an image transfer surface of the test material substantially parallel to the x axis of the elliptically collimated source beam and substantially orthogonal to the z axis of the elliptically collimated source beam;
   collecting image radiation emitted from the irradiated volume in the test material and transmitted through the image transfer surface by an optical imaging system;
   forming an image at a fixed image plane with the optical imaging system by aligning an object plane thereof conjugate to the image plane thereof at a central axis of the irradiated volume in the test material;
   maintaining an object depth of focus of the optical imaging system at a value that is approximately at least 1/5 of a radius along the z axis of the elliptically collimated source beam in the x axial collimation region; and
   recording the image formed by the optical imaging system in the image plane.

14. The method according to claim 13, wherein said collecting image radiation emitted from the irradiated volume in the test material and transmitted through the image transfer surface by an optical imaging system comprises collecting an image radiation emitted by one of scattering, luminescence and blackbody emission from the irradiated volume in the test material.

15. The method according to claim 13, wherein said recording the image formed by the optical imaging system in the image plane is done with one of a camera and an image recording means.

* * * * *